United States Patent [19]

Gross

[11] Patent Number: 4,723,557

[45] Date of Patent: Feb. 9, 1988

[54] LORDOSIMETER

[75] Inventor: Clifford M. Gross, New York, N.Y.

[73] Assignee: Hospital for Joint Diseases Orthopedic Institute, New York, N.Y.

[21] Appl. No.: 873,823

[22] Filed: Jun. 6, 1986

Related U.S. Application Data

[63] Continuation of Ser. No. 538,168, Oct. 3, 1983, abandoned.

[51] Int. Cl.[4] ............................................... A61B 5/10
[52] U.S. Cl. ..................................................... 128/787
[58] Field of Search .................... 128/774, 787 E, 782; 33/1 CC, 1 PT

[56] References Cited

U.S. PATENT DOCUMENTS

| | | | |
|---|---|---|---|
| 3,336,917 | 8/1967 | Pile et al. ............................. | 128/781 |
| 4,249,314 | 2/1981 | Beck ................................. | 33/1 PT X |
| 4,477,973 | 10/1984 | Davies ................................. | 33/1 CC |

FOREIGN PATENT DOCUMENTS

| | | | |
|---|---|---|---|
| 64788 | 11/1982 | European Pat. Off. ............ | 128/782 |
| 48310 | 10/1983 | European Pat. Off. ............ | 128/774 |
| 736957 | 6/1980 | U.S.S.R. .............................. | 128/782 |

OTHER PUBLICATIONS

Chao et al., "Instrument Measurement of Human Joint Motion", ISA Transactions, vol. 17, No. 1, (1978), pp. 13–19.
Yovm et al., "Accumla Data Collection Method . . .", Jrnl. Bioeng., vol. 2, pp. 359–367, 6/1978.
Panjabi et al., "A Technique for Measurement . . .", J. Biomech., vol. 14, No. 7, pp. 447–460, (1981).

*Primary Examiner*—Edward M. Coven
*Attorney, Agent, or Firm*—Stephen E. Feldman

[57] ABSTRACT

A spinal anthropometer or lordosimeter is described that provides a three dimensional configuration of the spine. Point encodement and codement of spacial measurement of spinal landmarks provides data permitting representation of spinal curvatures for diagnosis and assessment of lordosis and scoliosis.

2 Claims, 10 Drawing Figures

U.S. Patent  Feb. 9, 1988  Sheet 1 of 4  4,723,557
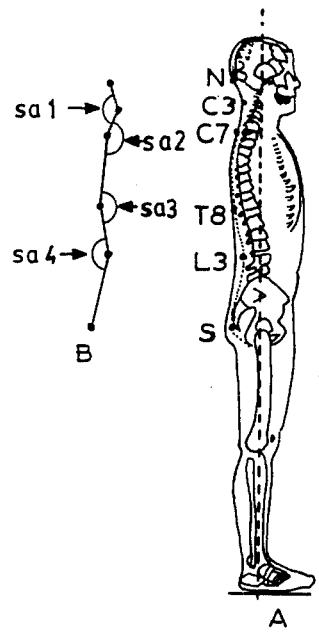
FIG. 2
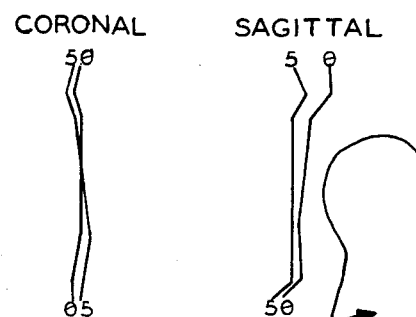
FIG. 4
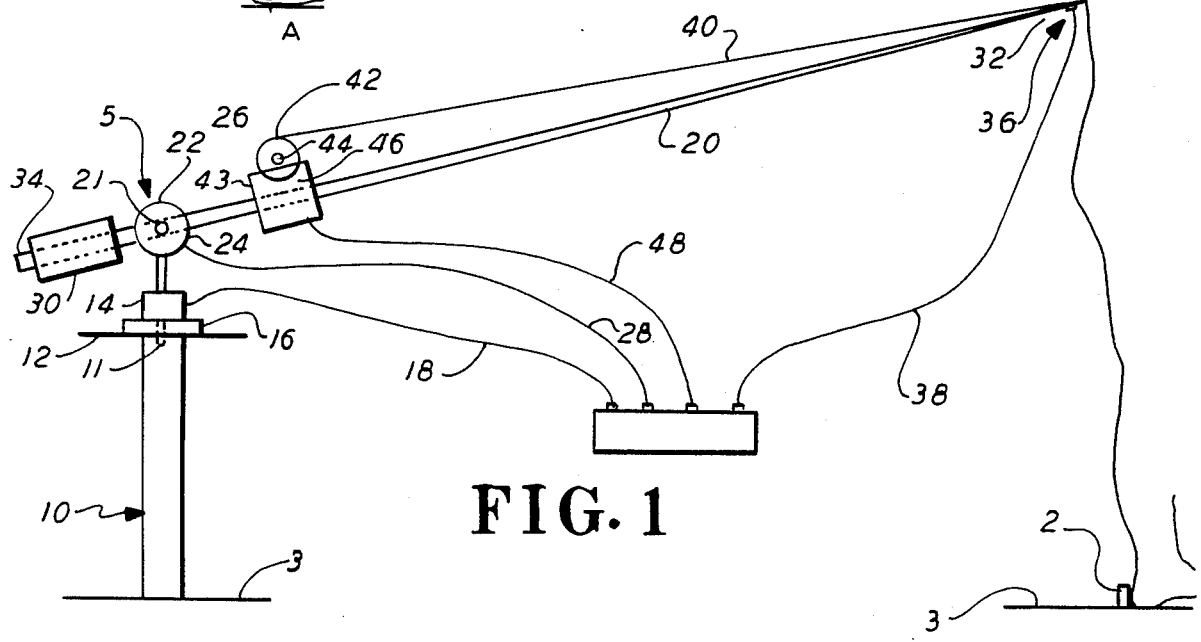
FIG. 1
FIG. 3
FIG. 5

```
10  Q = 0
20  INPUT "TODAY'S DATE"; G$
30  INPUT "SUBJECT'S NAME"; NA$
40  INPUT "HEIGHT IN INCHES"; D
50  INPUT "WEIGHT IN POUNDS"; F
60  K = (F*1000) / (D*D*D)
70  INPUT "ENTER 1 IF SUBJUCT IS NOR-
    MAL, 2 IF SCOLIOTIC"; AB
80  IF AB=2 THEN INPUT "1 FOR MAJOR,
    2 FOR DOUBLE MAJOR"; AC
90  POKE 3,1
100 PRINT TAB (29) "HOSPITAL FOR
    JOINT DISEASES"
110 PRINT TAB (32) "ORTHOPAEDIC
    INSTITUTE"
120 PRINT TAB (29) "DIVISION OF
    BIOENGINEERING"
130 PRINT: PRINT: PRINT: PRINT: PRINT:
    PRINT
140 PRINT "NNNNNNNNNNNN NNNNNN
    START OF RUN NNNNNNNNNNNNNN NN"
150 IF AB=2 THEN PRINT "PATIENT
    HAS SCOLIOSIS"
160 IF AC=2 THEN PRINT "WITH A
    DOUBLE MAJOR CURVE"
170 IF AC=1 THEN PRINT "WITH A
    SINGLE MAJOR CURVE"
180 IF AB=1 THEN PRINT "SUBJECT
    IS NORMAL"
190 POKE 3,0
200 PRINT "HOW MANY DATA POINTS"
210 INPUT N
220 POKE 3,1: PRINT "DATE:"; G$
230 PRINT N, "DATA POINTS ENTERED"
240 PRINT "SUBJECT"; NA$
250 PRINT "WEIGHT ="; F; "POUNDS"
260 PRINT "HEIGHT ="; D; "INCHES"
270 PRINT "SOMATYPE FACTOR K ="; K
280 POKE 3,0
290 DIM X (N), Y (N), Z (N)
300 PRINT
310 PRINT "ENTER DATA"
320 Q = Q + 1
330 IF Q=1 THEN POKE 3,1: PRINT
    "PRELOAD SPINAL TRACE"
340 POKE 3,0
350 POKE 3,1: IF Q=2 THEN PRINT "STATIC
    LIFTING TRACE"; (Q-1): POKE 3,0
360 PRINT
370 FOR I = 1 TO N
380 OUT & HFA, 255: WAIT & H18,I,I: OUT
    & HFA, 0
390 R(I) = INP (& H19)
400 IF R(I) > 128 THEN R(I) = R(I)-256
410 R(I) = R(I) + 128
420 R(I) = R(I) / 19.6153
430 R(I) = R(I) + 41
440 T(I) = INP (& H1A)
450 IF T(I) > 128 THEN T(I) = T(I)-256
460 T(I) = T(I) / -12.8
470 T(I) = T(I) * .017452
480 P(I) = INP (& H1B)
490 IF P(I) > 127 THEN P(I) = P(I)-256
500 P(I) = P(I) + 128
510 P(I) = P(I) / 5.12
```

FIG. 6a

```
520 P(I) = 50 - P(I)
530 P(I) = P(I) * .017452
540 Y(I) = R(I)*SIN (P(I))
550 X(I) = R(I)*SIN (T(I))*COS (P(I))
560 Z(I) = R(I)*COS (T(I))*COS (P(I))
580 PRINT "X"; I; "Y"; I; "Z"; I
590 POKE 3,1
600 PRINT "X("; I; ") ="; X(I); " Y("; I; ") =
    "; Y(I); " Z("; I; ") ="; Z(I)
610 POKE 3,0
620 POKE 3,0
630 NEXT I
640 W = 1
650 FOR J = 2 T (N-1)
660 POKE 3,1
670 IF W=2 THEN PRINT "SAGITTAL
    PLANE VIEW"
680 IF W=1 THEN PRINT "CORONAL
    PLANE VIEW"
690 H = (X(J-1) - X(J)) ↑ 2
700 K = (Y(J-1) - Y(J)) ↑ 2
710 A = (H+K) ↑ .5
720 L = (X(J) - X(J+1)) ↑ 2
730 M = (Y(J) - Y(J+1)) ↑ 2
740 B = (L+M) ↑ .5
750 P = (X(J-1) - X(J+1)) ↑ 2
760 O = (Y(J-1) - Y(J+1)) ↑ 2
770 C = (P+O) ↑ .5
780 X = (A↑2 + B↑2 - C↑2) / (2*A*B)
790 IF ABS(X+1) < 1E-06 THEN T =
    180: GOTO 850
800 T = -ATN(X/(-X*X+1) ↑.5) + 1.5708
810 T = (180*T) / 3.14159
820 POKE 3,0
830 IF W<1 THEN 870: IF W>2 THEN 870
840 POKE 3,0
850 PRINT "ANGLE AT POINT"; J; " =
    "; DEGREES"
860 POKE 3,1: PRINT "ANGLE AT
    POINT"; J; " ="; T; "DEGREES"
870 PRINT: POKE 3,0
880 NEXT J
890 W = W + 1
900 FOR I = 1 TO N
910 IF W = 2 THEN X(I) = R(I)*COS(T(I))
    *COS (P(I))
920 NEXT I
930 IF W = 2 THAN GO TO 650
940 PRINT "SHALL WE RUN IT AGAIN";
950 PRINT
960 INPUT W$
970 IF LEFT$(W$,1) = "Y" THEN 300
980 POKE 3,1
990 PRINT "............................"
1000 POKE 3,0
1010 PRINT "DO YOU WANT TO RECORD
     A POLYNOMIAL OF THE SPINE";
1020 INPUT Z$
1030 IF LEFT$(Z$,1) = "Y" THEN LOAD
     "POLLY 3B BAS", R
1040 POKE 3,1
1050 PRINT "END OF RUN": POKE 3,0
```

FIG. 6b

```
1    PRINT"THE FOLLOWING PROGRAM
     PLOTS SPINAL CONFIGURATION":
     IF ZZ = 2 GO TO 9800
2    PRINT"ENTER PATIENT'S INITIALS"
3    INPUT P$
4    PRINT"ENTER NORMAL OR
     SCOLIOTIC"
7    INPUT N$
11   Z$ = CHR$ (69)
50   C$ = CHR$ (27)
60   A$ = CHR$ (65)
70   O$ = CHR$ (70)
71   PRINT C$;A$;O$
85   S$ = CHR$ (73)
92   PRINT TAB (20)"ENTER THE 12 X,
     Y, Z COORDINATES TO BE PLOTTED"
93   N=2
94   PRINT TAB (20)"------------------"
102  FOR I = 1 TO N
103  PRINT"ENTER X(";I;")";"Y(";I;")";"Z(";I;")"
106  INPUT X(I),Y(I),Z(I)
107  NEXT I
108  PRINT "IS THE DATA CORRECT?":IN-
     PUT Y$: IF Y$="YES"THEN GOTO 109
     ELSE GOTO 1:ERASE
109  FOR I = 1 TO 1000:AA=I*I*I NEXT
     I:GOSUB 1000
110  PRINT C$; A$; O$
113  FOR I = 1 TO N
121  Z(I) = (Z(I) - 15)*20
122  X(I) = (X(I) + 10)*20
123  Y(I) = Y(I)*20
124  NEXT I
125  PRINT C$;A$;Z$
126  DRAW X(1)- 50, Y(1) + 50,0
128  PRINT"CORONAL"
179  PRINT C$; A$; Z$
180  DRAW X(1)-5,Y(1)-5,0:PRINT"O"
185  PRINT C$; A$; Z$
186  DRAW X(1),Y(1),0
188  FOR I = 2 TO 6
300  DRAW X(I),Y(I),1
310  IF I=6 THEN DRAW X(I)-5,Y(I)-5,
     0:PRINT "O"
311  NEXT I
312  IF I = 7 THEN DRAW X(7),Y(7),0
315  DRAW X(7)-5,Y(7)-5,0 :PRINT "5"
316  DRAW X(7),Y(7),0
350  FOR I = 7 TO 12
352  DRAW X(I),Y(I),1
353  IF I = 12 THEN DRAW X(I)-5,Y(I)
     -5,0:PRINT"5"
354  NEXT I
410  GOTO 3000
1000 PRINT C$; A$;Z$
1001 DRAW 0,0,0
```

FIG.7a

```
1002 DRAW 0,700,1
1003 DRAW 1000,0,0
1004 DRAW 0,0,1
1010 DRAW 700,700,0:PRINT"THE
     SUBJECT IS;";N$
1020 DRAW 700,680,0:PRINT"INITIALS;"
     ; P$
1050 DRAW 100,750,0:PRINT"THREE
     DIMENSIONAL LORDOSIMETRY"
1060 DRAW 700,100,0
1061 DRAW 700-5, 100-5,0:PRINT"\!"
1062 DRAW 700,100,0
1063 DRAW 720,100,1
1064 DRAW 720-5,95,0:PRINT"\! =
     1 INCH"
1067 DRAW 720,120,0:PRINT "SCALE"
1080 DRAW 720,200,0:PRINT " KEY "
1082 DRAW 700,180,0:PRINT"O=PRELOAD"
1083 DRAW 700,160,0:PRINT"5=5 LB.
     STATIC LOAD"
2000 PRINT C$ ; A$ ; O$
2001 RETURN
3000 DRAW Z(1)-50, Y(1) +50,0
3002 PRINT "SAGITTAL"
5030 DRAW Z(1)-5,Y(1)-5,0:PRINT"O"
5040 DRAW Z(1),Y(1),0
5060 FOR I = 2 TO 6
5080 DRAW Z(I),Y(I),1
5085 IF I= 6 THEN DRAW Z(I)-5, Y(I)
     -5,0:PRINT"O"
5090 NEXT I
6000 IF I=7 THEN DRAW Z(7),Y(7),0
7000 IF I=7 THEN DRAW Z(7)-5, Y(7)-
     5,0:PRINT "5"
7001 DRAW Z(7),Y(7),0
7500 FOR I=7 TO 12
8000 DRAW Z(I),Y(I),1
8500 IF I=12 THEN DRAW Z(I)-5,Y(I)-
     5,0:PRINT"5"
9000 NEXT I
9002 PRINT C$;A$; O$;
9500 ZZ = 2
9800 PRINT"WOULD YOU LIKE AN-
     OTHER PLOT?"
9810 INPUT L$
9811 IF L$="NO"THEN ZZ=0: IF L$ =
     "NO" THEN END
9820 IF L$="YES"THEN GOTO 9821
9821 PRINT"IS THE PLOTTER PAPER
     IN PLACE?"
9822 INPUT LL$
9824 IF LL$="YES" THEN ERASE ELSE
     9821
9826 GOSUB 1000:GOTO 125
```

FIG.7b

THREE-DIMENSIONAL PLOTTING PROGRAM

```
1   a=30:b=0:m=20:d=90:e=90;f=10
2   if 1 =1 goto 310
3   print"ENTER SUBJECT'S NAME,NORMAL OR SCOLIOTIC"
4   input n$,s$
5   n= 6
6   c$= chr $ (27)
7   a$= chr $ (65)
8   o$= chr $ (70)
9   z$= chr $ (69)
10  for i=1 to n
11  dim x (n), y (n), z (n)
30  print "enter x (";i;"),y (";i;"),z (";i;")"
48  input  y(i),z(i),x(i)
49  x(i) = - x (i)
50  next i: erase
51  for i = 1 to n
52  x(i) = x (i) - x (6)
53  y(i) = y (i) - y (6)
54  next i
55  dd = 0
56  for i = 1 to n
57  x (i) = m * x (i) : y (i) = m * y (i) : z (i) = m * z (i)
58  next i
59  print c$ ; a$;z$
60  for t =0 to e step f
61  t = t * .01745329
62  dd = dd + 1
100 for i = 1 ton
170 y 2 (i) = sin (t) * x (i) + cos (t) * y (i)
172 next i
174 i = 1
178 for i = 1 to 6
180 if t=0 then goto 181 else 183
181 if i=1 then draw y 2 (1) +a+dd * d - 40, z (1) +b+ 20,0 : print    "CORONAL"
183 if i=1 then draw y 2 (1) +a+dd * d - 5 , z (1) +b -5,0 ; print  "0"
184 if i=1 then draw y 2 (1) +a+dd * d , z (1) + b , 0
186 if i = 7 then draw y2(i) +a -5, z (i)+ b + 5,0 : print"5"
187 if i = 7 then draw y2(i) +a,z (i) + b,0
188 if int (t*57.2957795131+.01 = 90 then goto189 else 200
189 if i = 1 then draw y2 (1)+ a+dd*d-55,z (1) +b+20,0 :print "SAGITTAL"
190 if i = 1 then draw y2 (1) +a+dd*d ,z (1) +b , 0
200 draw y2 (i) +a +dd*d,z (i) +b,1
202 if i = 6 then  draw y2 (6) +a +dd*d-5,z (6) +b-5,0:print"0"
203 if i = 12 then draw y2 (i) +a-5, z (i) + b-5,0:print "5"
204 t = 57.2957795131*t
205 if i = 6 then draw y2 (6) + a +dd *d - 30,z (6) +b-35 ,0:print int (t+ .001)
206 if i = 6 then draw y2 (6) + a+ dd*d + 7,z (6) +b- 20,0 :print "0"
240 t = t / 57.2957795131
250 next i
251 t = t / .01745329
```

FIG. 8

LORDOSIMETER

This application is a continuation of application Ser. No. 538,168, filed Oct. 3, 1983, now abandoned.

FIELD OF THE INVENTION

This invention relates to anthropometers and more particularly to anthropometers specifically designed to measure spinal parameters for diagnosis and assessment of lordosis and scoliosis.

BACKGROUND OF THE INVENTION

Anthropometry is the science of measuring the shape of the spine and the effect of loads on the spine. One of the results of such measurements is a positive diagnosis of scoliosis and lordosis. These are conditions resulting from displacement from the normal of the spinal vertabrae. Lordosis is defined as the anteriorposterior malposition of the spinal processes whereas scoliosis is the lateral malposition thereof.

Live body anatomical measurements, particularly relative spinal position measurements fall into three categories, in vivo measurements; radiological measurements and surface mapping relative to anatomical reference points.

Three-dimensional computer-aided x-ray analysis of the human spine was reported by Shu in 1974 (J.Biomech 7,161-169). Variations were developed by Kraty in 1975 (Photogrammatica 31: 195-210) and Brown et al in 1976 (J.Biomech 9: 355-365).

Kraty located and recorded the transverse and spinous processes of each vertabra in both frontal and lateral projections and built up projection from triangles formed by connecting the transverse and spinous processes. These were extended by further connection to form polygons. This technique presented problems in patient movement during repeated repositioning of the x-ray machine.

Brown et al recorded bi-planar x-rays with a reference frame provided by radio-opaque indices embedded in Plexiglass panels located between the x-ray sources and the film. Each vertabra was thus modeled as a tetrahedron whose four vertices were the two pedicles and the superior and inferior vertabral body centers. The location data on each vertabra was digitized and the determination of the extent of curvature was made and compared with a manual determination on lateral x-ray. The angles compared favorably within 5 degrees. Projections were also plotted for visual assessment.

A study of the configuration of the spine in response to static loading was reported by Tichaner et al (J.Am Industr. Hyg Assn 34: 4(1973)) and named Lordisometry. This employed a two dimensional measuring device which consisted of two aluminum rods each hinged to an upright support. The angular displacement of each rod was measured by a sine-cosine potentimeter mounted at each hinge.

The potentimeter outputs, after electronic enhancement, were converted to X and Y coordinates of each point measured and plotted on an X-Y recorder. The reference points selected were the tip of the sacrum, L3, T8, C7, C3 and the midpoint of the superior nuchal line. From the coordinates of these points, the cervico-occipital, thoracocervical, lumbothoracic, lumbosacral and sacral angles relative to the horizontal were calculated and assessed.

A tracer for mapping anatomical surfaces for the study of carpal tunnel syndrome was developed by Armstrong et al (J.Biomech 12: 397(1979)). This mapper consisted of two orthogonally mounted linear potentiometers which rotated freely about a linear differential voltage transformer. Encoded points in space were scaled and represented as spherical coordinates. These coordinates were then converted to Cartesian coordinates, stored on a diskette and plotted. This device permitted the representation of the flexor digitorum profundus tendon (of the second digit) in flexed, intermediate and extended positions.

Gold et al as reported by Tichauer had demonstrated (17th Conference American Assoc. for Automotive Medicine at Oklahoma City OK Nov. 73) a three-axis kinesiometer which provided displacement, velocity and acceleration signatures of hand guided objects in space.

The apparatus consisted of three coplanar linear potentiometers located at the vertices of a right triangle mounted perpendicular to the task board. A pulley was mounted on the shaft of each potentiometer in conjunction with a spring-activated take up wheel. This provided constant tension in the string that was wrapped around each pulley. All three of the strings were connected to a ring which was fitted to a finger of the active hand being measured. This permitted a point by point determination of the instantaneous displacement, along with its first and second derivatives. The device was sufficiently sensitive to reproduce dangerous motion patterns and tremors.

Recently thermography has been used, Cooke et al (Clin. Orthop. 148: 172-176, 1980)), to detect minor scoliotic curvatures based on the asymmetry in spinal infra-red emission due to slightly asymmetric blood flow in scoliotic individuals. While theoretically viable, problems of calibration temperature control, equipment cost etc. militate against this method.

Moire topology has also been investigated for non-radiographic scoliosis screening by Wilner (Orthop.Scand. 50: 295 (1979)). The basic technique consists of producing interference patterns from a 1000 watt point source on the back of a subject standing in front of a vertical wire screen consisting of strands of 1 mm black nylon wire spaced 1 mm apart.

The interference of the light projected through the screen produces contour lines (shadows) at given distances from the screen on the subject's back. The contours are analagous to a topographical map with each contour proportional to the elevation of the back relative to the screen. Though slight asymmetries are detectable, fringe difference as related to Cobb angle, yield a rather large scatter. For this reason assessment of curvature progression over time with this technique is doubtful. However this method would be very useful in school screening programs. Such programs have been demonstrated as potentially effective.

Though radiography is capable of thoroughly documenting spinal geometry, the hazards associated with x-ray exposure are well-known.

Thermography and Moire topology may be of value in screening programs for scoliosis. However, neither of these techniques is able to quantify, at present, lateral displacement nor have measurements been taken to relate such displacement to underlying anatomical reference points for adequate mapping to determine subsequent progression or recession (and cure).

The Invention

The present invention is based upon the analysis from the above that three-dimensional anthropometry allows for the simple gathering of spherical coordinates from various points of the body permitting the screening, diagnosis and assessment of lordosis and scoliosis.

The device of this invention may be traced in origin to the combined principal of operation of the triaxial kinesiometer of Gold et al with the two dimensional lordisometer of Tichauer as described above. However, the manner of combining these operations and their application in the form of a simple device which provides direct interpretation of the clinical measurements for proper diagnosis and assessment of scoliosis and lordosis is unforeseen.

The device of this invention is a three-dimensional anthropometer (also alternately denoted as a combined lordisometer and scoliometer) for use in the screening and diagnosis of lordosis and scoliosis and assessing the degree of such conditions, which comprises a telescopic steel rod mounted in a fixed housing. The telescopic rod is extendable from said housing and is fitted at its distal end with a body contacting point and is connected in said housing at its proximate end to the vertex of two orthogonally mounted linear potentiometers. Displacement of said orthogonal mounting provides analog signals generated in said potentiometers indicating azimuth and elevation. A third linear potentiometer, mounted on said housing, is connected by a nylon string wrapped around a pulley and to the extensible end of the telescopic rod whereby an analog signal is generated from said third potentiometer by rotation of said pulley during passage of the nylon cord upon extension of said rod. The potentiometers are each powered by a regulated power supply. The analog signal outputs of each of said potentiometers being linearly amplified to the range of measurements of spinal positional parameters: said amplified analog signals representing elevation, azimuth and extension with respect to the fixed position of said device and the measured spinal points. The respective signals are then digitized by appropriate electronic circuits and the thus digitized signal is converted by an appropriate algorithm from the initially derived spherical coordinates to Cartesian coordinates defining the coronal and sagittal plane spinal angles. These angles, derived from the various measured points, are related to each other and their relationship is useful for the diagnosis and assessment of the conditions of scoliosis and lordosis.

A microprocessor-based data acquisition system programmed with the appropriate algorithm is utilized for calculating the sagittal and coronal plane spinal angles and then relating these derived data to angles found in normal subjects; graphically representing these relationships so that comparisons may be made and a proper diagnosis and assessment derived.

In practice the data is derived by identifying six anatomical landmarks on the subject. These landmarks are the inion (midpoint of the superior nuchal line), the third cervical spinous process, the seventh cervical spinous process, the third lumbar spinous process, and the second sacral process. For ease of measurement these are marked on the subject. Then repetative traces are recorded of these six anatomical landmarks with the subject standing erect on a foot position graticule with arms extended and holding a light paper tube. The traces are recorded by extending and positioning the telescopic tube to contact the marked landmarks on the subject. Upon contact, a pressure activated switch activates the encoding of the coordinates of the spatial points of the landmarks by the three voltages from the potentiometers r, $\theta$ and $\phi$ which are subsequently converted into the X,Y and Z cooridinates, locating each landmark in three-dimensional space with respect to the fixed base of the device and the graticle upon which the subject is standing.

The digitized voltages, encoded into the microprocessor, are called up by the algorithm (a Wait statement in a Basic program) which converts the voltage from spherical to cartesian coordinates.

To provide visual assessment of the sagittal and coronal postural adjustments during loading, plots of the digitized spinal traces are also made while the subject was holding a five pound weight instead of the paper tube. The spinal trace was also recorded in a 3-dimensional 90° rotation so that a full evaluation in both anteriorposterior as well as lateral planes is available.

BRIEF DESCRIPTION OF THE DRAWING

Details of the device of the invention and its use in the practice of this invention will be set forth below and in the associated Drawing wherein FIG. 1 is a plan view of the spinal anthropometer of the invention making measurements on a subject;

FIG. 2 is a representation of the anatomical reference points of subjects that are measured in the practice of the invention and their included angles in the sagittal plane;

FIG. 3 has plots of the coronal and saggital planes of a normal subject before and during lift of a five pound load;

FIG. 4 has plots of the coronal and saggital planes of a scoliotic subject before and during lift of a five pound load.

FIG. 5 is a three dimensional spinal plot for a normal subject varying from coronal aspect $\phi=0°$ to the sagittal aspect $\phi=90°$;

FIGS. 6a and 6b are a typical Data Acquisition program or algorithm in Basic machine language presented in a manner suitable for input into computers or microprocessors equipped with an Optical Character Reader (OCR);

FIGS. 7a and 7b are an OCR-ready program for Coronal and Sagittal Plane Spinal Plotting and;

FIG. 8 is an OCR-ready program for three-dimensional plotting to yield representations similar to those of FIG. 5.

DETAILED DESCRIPTION

Referring now to FIG. 1, the subject 1, is positioned by a foot graticle 2 on floor 3, a fixed distance from the spinal three-dimensional anthropometer 5 of this invention. The anthropometer is mounted on fixed base 10 at a convenient level above floor 3. On base 10 is mounted support 11 which is also the azimuth pivot 11 located centrally to azimuth plate 12 marked at its periphery with azimuth angles. Azimuth pivot 11 is coupled to azimuth reading potentiometer 16 by azimuth bearing 14 so that changes in position of pivot 11 with respect to the potentiometer 16 will modify the signal generated therein.

Affixed to azimuth pivot 11 is telescopic rod 20 so that movement thereof in the horizontal plane will provide changes in the azimuth angle $\theta$ and resultant azimuth potentiometer 16 signals. The signals are conducted from the potentiometer via lead 18 to junction box 50 which is the input portal to the computer or processor (not shown).

The mounting of telescopic rod 20 to pivot 11 is near its proximate end. The mounting of the rod 20 to azimuth pivot 11 is via elevation pivot 21 linked to elevation plate 22 and elevation reading potentiometer 26 through elevation bearing 26. The derived elevation signal from elevation potentiometer 26 is led via elevation signal leads 28 to junction box 50, the input portal to the computing device (not shown).

Telescopic rod 20 is fitted with a balance weight (or counter weight) 30 at its proximate end 34, to permit ease of rotation of rod 20 around pivot 21. At distal end 32 of rod 20 is locating pointer 35 for contact with the landmark points on patient 1 during the mapping and measuring procedure. Locating pointer 35 is fitted with switch 36 and leads 38 therefrom to junction box 50. A nylon chord 40 runs from locating pointer 35 at the distal end 32 of telescopic rod 20 to the extension indicating assembly 41 consisting of extension pulley 42 around which chord 40 is wound, extension pulley pivot 44 which actuates extension reading potentiometer 46, and the nylon chord take-up mechanism 47. Mechanism 47 may be spring or weight loaded to ensure proper tension on pulley 42 without interfering with the actuation of the extension mechanism of telescopic rod 20. The signal from extension reading potentiometer 46 is fed by leads 48 to junction box 50, the computer input.

When locating pointer 35 is properly located in juxtaposition with the landmark point on subject 1, switch 36 is activated to signal the computer to record and process the signals from each of the azimuth potentiometer 16, elevation potentiometer 26 and extension potentiometer 46.

In practice the potentiometer reading signal from each of the potentiometers 16, 26 and 46 is amplified between the junction box and the computer. Depending on the computer, the amplified signals are digitized either by separate digitizer chips external or internal to the computer.

The degree of amplification of the potentiometer outputs, varied from a regulated 5 volt input, should be such as to scale the voltages for the range of the device [(0°–50° elevation ($\theta$), ±10° azimuth ($\phi$), 0–12 inches (r)] and the usual allowable input of analog/digital (a/d) converters (±2.5 volts).

FIG. 2 shows the anatomical references points used in mapping the spinal shapes of the subjects. Their angles in the sagittal plane is also shown.

Table I names these landmarks and lists the abbreviations therefor shown in the FIG. 2.

TABLE I

| | |
|---|---|
| Inion (midpoint of superior nuchal line) | N |
| Third cervical spinous process | $C_3$ |
| Seventh cervical spinous process | $C_7$ |
| Eighth Thoracic spinous process | $T_8$ |
| Third Lumbar spinous process | $L_3$ |
| Second sacral process | S |

Table II lists the names and abbreviations for the spinal angles derived from the positional measurements of the landmarks listed in Table I.

TABLE 2

NAMES AND ABBREVIATIONS FOR SPINAL ANGLES

| | |
|---|---|
| Sagittal Plane Angles | |
| cervical-occipital angle | SA1 |
| thoraco-cervical angle | SA2 |
| lumbo-thoracic angle | SA3 |
| lumbosacral angle | SA4 |
| Coronal Plane Angles | |
| cervical-occipital | CA1 |
| thoraco-cervical angle | CA2 |
| lumbo-thoracic angle | CA3 |
| lumbosacral angle | CA4 |

FIGS. 3, 4 and 5 are plots of the derived angles from the mappings of the landmarks in FIG. 2 and Table I for various subjects under unstressed and loaded conditions. The subjects were diagnosed as normal or scoliotic and the effects of the clinical condition of scoliosis is clearly apparent from the plots of FIG. 4 as compared to the plots in FIG. 3. The rotational plot in FIG. 5 is particularly useful in differentiating clinical scoliosis compounded by lordosis.

A further exposition of the use of the device of this invention in diagnostic screening is found in Gross et al: (Bull.Hosp.for Joint Diseases, Orthopedic Inst. Vol. XL11 #2 (Fall, 1982) Pages 151–171).

FIGS. 6–8 are presented for the convenience of practioners using the device of this invention is conjunction with computers or microprocessors accepting processing instructions in Basic. These programs are presented in a format suitable for reading by Optical Character Readers such as manufactured by Hendrix Corp. for acceptance and entry into the processing memory. FIG. 6 handles the storage of the data acquired from mapping each of the landmark points for use in later manipulation. Such manipulation, in addition to the recording and tabulating of the data, includes manipulation to plot the coronal and sagittal planes of the mapped spines and their angles under normal and stressed conditions as shown in FIGS. 3 and 4. Such plotting instructions are shown in the program of FIG. 7. Such plotting permits observation of aberations from the normal, leading to ease of diagnosis of the conditions being screened.

FIG. 8 provides a program in machine readable form for additional useful manipulation of the data stored by the program of FIG. 6.

A useful microprocessor that has been used with the programs of FIGS. 6–8 was manufactured and sold as the SOL microcomputer. It is no longer available but these programs have also been used on the TR-80 microcomputer sold in the USA by the Radio Shack stores. The aforementioned article by Gross et al includes examples of screening and calibration results. The programs of FIGS. 6–8 are reproduced from said article which is included herein by reference to show further aspects and uses of this invention.

The invention, as above described, is not limited by the specific embodiments disclosed but includes all equivalents thereof. Such equivalents include mapping of the coordinates of the landmarks by optical means equivalent to the mechanical devices described. Utilizing other coordinate measuring means than the potentiometer described including sonic locators and optical locators.

While one specific embodiment has been described in detail and equivalent embodiments have been sufficiently alluded to, it is obvious that many modifications to the embodiments described and mentioned may be made without departing from the scope and spirit of this invention.

What is claimed is:

1. A three-dimensional direct reading anthropometer useful in diagnosis and evaluation of lordosis, scoliosis and other spinal disformations in humans, said anthropometer producing a three-dimensional curvature of the spine, comprising;
   (a) a base;
   (b) a support mounted on said base which functions as an azimuth pivot;
   (c) an azimuth measuring means comprising an azimuth reading potentiometer connected to said azimuth pivot, so that changes in the position of said azimuth pivot can be registered for obtaining azimuth data of a point on the human body, an azimuth plate marked at its periphery with azimuth angles, said plate located centrally to said azimuth pivot, and an azimuth bearing coupling said azimuth pivot to said azimuth reading potentiometer;
   (d) an extendable rod connected to said azimuth pivot, said rod having a pointer means for contacting chosen points on the human body, said extendable rod being a telescopic rod comprising an elevation pivot linked to an elevation plate, said elevation pivot linking said rod to said azimuth pivot and a balance weight mounted on the proximate end of said rod, said weight permitting rotation of said rod around said elevation pivot, and said point means comprises a locating pointer for making contact with predetermined points on the human body, said pointer including a switch having a first position and a second position, actuated from said first position to said second position when said locating pointer is placed on one of said predetermined points, said switch for energizing said potentiometer when in said second position, and a cord extending from said locating pointer at a distal end of said telescopic rod to an extension-indicating assembly comprising an extension pulley, around which said cord is wound;
   (f) an extension measuring means comprising an extension reading potentiometer connected to said extendable rod for obtaining data on the same point on a body, an extension pulley pivot actuating said extension reading potentiometer, and a cord rewind means for causing a proper tension on said pulley without interfering with actuation of said extension measuring means;
   (g) means coupled between said potentiometers and a computer means for receiving signals generated by said potentiometers and for applying said signals to said computer means said means for receiving signals including amplifier means for amplifying the signals received from said potentiometers before said signals are applied to said computer means; and
   (h) said computer means include analog to digital converter means for converting analog signal data received from said means for receiving into corresponding digital signal data, and said computer means plots the digital signal data for displaying information defining the point on the human body.

2. A method for diagnostic screening of spinal curvatures comprising the steps of:
   (a) positioning the subject at a fixed distance from a three-dimensional anthropometer for producing a three-dimensional curvature of the spine, said anthropometer comprising a base, a support which is also an azimuth pivot, mounted on said base; an azimuth measuring means comprising an azimuth reading potentiometer connected to said azimuth pivot, so that changes in the position of the azimuth pivot can be registered, said azimuth measuring means also comprising an azimuth plate marked at its periphery with azimuth angles, said plate located centrally to said azimuth pivot and an azimuth bearing coupling said azimuth pivot to said azimuth reading potentiometer; an extendable rod connected to said azimuth pivot, said rod having a pointer means to contact landmark points on the human body, said extendable rod being a telescopic rod which further comprises an elevation pivot linked to an elevation plate, said elevation pivot linking said rod to said azimuth pivot, and a balance weight mounted on the proximate end of said rod; an elevation measuring means comprising an elevation reading potentiometer connected to said rod, said weight permitting an ease of rotation of said rod around said elevation pivot; an extension measuring means comprising an extension reading potentiometer connected to said rod; a pointer means comprising a locating pointer for contacting with landmark points on a human body said pointer being fitted with a switch said switch activated when the locating pointer is placed on one of said landmark points; a cord running from said locating pointer at a distal end of said telescopic rod to an extension-indicating assembly comprising an extension pulley, around which said cord is wound, an extension pulley pivot actuating an extension reading potentiometer, and a cord take-up mechanism insuring proper tension on said pulley without interference with the actuation of said extension measuring means; means for receiving signals from said potentiometers and for sending said signals to a computer; a computer able to digitalize said signals;
   (b) contacting said subject with said rod at said landmark points;
   (c) turning on said switch located on said locating pointer, said pointer being part of said pointer means, when said subject is contacted with said locating pointer at said landmark points, said landmark points comprising an inion, a third cervical spinous process, a seventh cervical spinous process, an eighth thoracic spinous process, a third lumbar spinous process and a second sacral process; said anthropometer further comprising amplification means for amplifying signals from each of said potentiometers before applying said signals to said computer; and said means for receiving signals from said potentiometers comprise a junction box and leads connecting said potentiometers to said junction box;
   (d) recording and processing signals from each of said potentiometer on said computer said processing of signals comprising digitizing of voltages obtained from said potentiometer by a digital converter, said digitized voltages further being called up by an algorithm which converts the voltages from spherical to cartesian coordinates;
   (e) plotting the data obtained by said computer; and
   (f) diagnosing said subject based on analysis of said data.

* * * * *